(12) United States Patent
Van Wijck

(10) Patent No.: US 6,344,588 B1
(45) Date of Patent: Feb. 5, 2002

(54) PROCESS FOR THE PREPARATION OF UREA

(75) Inventor: Julius G. T. Van Wijck, Maastricht (NL)

(73) Assignee: DSM, N.V., Heerlen (NL)

( * ) Notice: Subject to any disclaimer, the term of this patent is extended or adjusted under 35 U.S.C. 154(b) by 59 days.

(21) Appl. No.: 09/607,325

(22) Filed: Jun. 30, 2000

Related U.S. Application Data

(62) Division of application No. 08/921,371, filed on Aug. 29, 1997, now Pat. No. 6,114,579.

(30) Foreign Application Priority Data

Aug. 30, 1996 (NL) ............................................. 1003923
Nov. 8, 1996 (NL) ............................................. 1004475

(51) Int. Cl.⁷ ..................... C07C 273/04; C07C 273/12
(52) U.S. Cl. ........................... 564/67; 544/201; 564/66; 564/69; 564/70; 564/71; 564/72; 95/241; 95/258; 95/263; 95/264; 95/265; 96/243
(58) Field of Search .............................. 564/66, 67, 69, 564/70, 71, 72; 544/201; 95/241, 258, 263, 264, 265; 96/243

(56) References Cited

U.S. PATENT DOCUMENTS

| | | | |
|---|---|---|---|
| 3,239,522 A | 3/1966 | Cook et al. .............. 260/249.7 |
| 3,700,672 A | 10/1972 | Kobubo et al. ....... 260/249.7 P |
| 3,708,536 A | * 1/1973 | Hillenbrand ............. 260/855 A |
| 4,433,146 A | 2/1984 | Beckers et al. ............. 544/201 |
| 4,565,867 A | * 1/1986 | Thomas et al. ............. 544/201 |
| 5,514,796 A | 5/1996 | Best et al. .................. 544/201 |

FOREIGN PATENT DOCUMENTS

| | | |
|---|---|---|
| CA | 724228 | 12/1965 |
| CA | 760462 | 6/1967 |
| EP | 0 329 214 | 2/1989 |
| GB | 1 216 100 | 12/1970 |
| GB | 1216100 | * 12/1970 |
| GB | 1 309 275 | 3/1973 |
| JP | 12911 | 6/1965 |
| JP | 12912 | 6/1965 |
| SU | 01747 | 1/1969 |
| SU | 01747 J/47 | * 1/1969 |

* cited by examiner

Primary Examiner—Peter O'Sullivan
(74) Attorney, Agent, or Firm—Pillsbury Winthrop LLP

(57) ABSTRACT

In the present process for the preparation of urea, an off-gas stream released during the synthesis of melamine in a high-pressure melamine process which consists predominantly of ammonia and carbon dioxide, is introduced into at least one high-pressure section of a urea stripping plant and is used in the synthesis of urea. The off-gas stream can be used directly without any further treatment.

6 Claims, 6 Drawing Sheets

Q = Flash vessel

R = Prestripper

PROCESS FOR THE PREPARATION OF UREA

This application is a divisional of U.S. patent application Ser. No. 08/921,371, filed Aug. 29, 1997, now U.S. Pat. No. 6,114,579.

BACKGROUND OF THE INVENTION

1. Field of the Invention

The present invention relates to a process for the preparation of urea in which the gas stream released from the process for making melamine, consisting predominantly of ammonia and carbon dioxide, is recovered and, without further treatment, used in the urea process in the synthesis of urea. More particularly, the recovered gas stream is fed to a high pressure section of a urea plant.

2. Description of Related Art

Urea can be prepared by introducing ammonia and carbon dioxide into a synthesis zone at a suitable pressure, for example 12.5–35 MPa, and at a suitable temperature, for example 160–250° C. Ammonium carbamate is formed first according to the following reaction:

$$2\ NH_3 + CO_2 \rightarrow H_2N\text{—}CO\text{—}ONH_4$$

Urea is subsequently formed by dehydrating the ammonium carbamate according to the following equilibrium reaction:

$$H_2N\text{—}CO\text{—}ONH_4 \leftrightarrow H_2N\text{—}CO\text{—}NH_2 + H_2O$$

The degree to which the latter conversion takes place depends on the temperature and the ammonia excess applied, among other factors. The solution obtained as the reaction product predominantly consists of urea, water, ammonium carbamate and unbound ammonia. The ammonium carbamate and the ammonia need to be removed from the solution. Once removed, they are typically returned to the synthesis zone. The synthesis zone may include separate zones for the formation of ammonium carbamate and urea. However, these zones may also be combined in one piece of equipment.

Urea can be prepared in a conventional urea plant. A conventional high-pressure urea plant is one in which the decomposition of the ammonium carbamate that has not been converted into urea and the expulsion of the usual excess ammonia are conducted at a pressure between 1.5 and 10 MPa which is essentially lower than the pressure in the urea synthesis reactor. The synthesis reactor is conventionally operated at a temperature of about 180° C. to about 210° C. and at a pressure of about 18 MPa to about 30 MPa. Ammonia and carbon dioxide are directly fed to the urea reactor. The $NH_3/CO_2$ molar ratio (N/C molar ratio) in the urea synthesis is generally between about 3 and about 5 in conventional high-pressure urea processes. The unconverted reactants are recycled, after expansion, dissociation and condensation, to the urea synthesis reactor.

A variant of a conventional process for preparing urea is described in GB-A-1309275. In the described process, off-gas, also commonly referred to as waste gas, obtained in the preparation of melamine in a high-pressure melamine process is used for the synthesis of urea. The melamine off-gas consists predominantly of ammonia and carbon dioxide. The off gas stream from the gas/liquid separator of the melamine plant is transferred via a scrubber only to a low-pressure section, i.e., a low pressure first urea synthesis section. In this low-pressure section, a urea solution is prepared in an extra reactor using the ammonia and carbon dioxide originating from the melamine plant. This urea solution is subsequently compressed and transferred to a high-pressure section of the same urea plant.

The process of GB-A-1309275 suffers from a number of drawbacks. An extra reactor is required because the pressure of the off-gas stream supplied from the melamine plant is too low, even when it originates from a high-pressure melamine process, to be used directly in a conventional high-pressure urea plant. Also, one or more extra pumps are required in order to transfer the urea produced in the first low pressure urea synthesis section to the high-pressure urea synthesis section(s).

Despite these and other efforts to effectively integrate urea and melamine production facilities, there remains a need for an industrially facile and less capital intensive process for the recovery and use of off or waste gases comprised of ammonia and carbon dioxide from a high pressure melamine plant directly in a high pressure urea plant.

SUMMARY AND OBJECTS OF THE INVENTION

The present invention offers an attractive solution to these and other industry-recognized needs by effectively utilizing an off-gas stream from a high-pressure melamine process directly in a high-pressure section of a urea stripping plant.

The off-gas stream from the high-pressure melamine process consists predominantly of ammonia and carbon dioxide. Predominantly means that more than 90 wt. % of the off-gas stream consists of ammonia and carbon dioxide, preferably more than 95 wt. %. Further the off-gas stream may contain small amounts of for example melamine, urea, isocyanic acid and/or hydrogen. The $NH_3/CO_2$ molar ratio in the off-gas stream is about 2 or higher, preferably between about 2.2. and about 4.

A high pressure section of the urea stripping plant can, for example, be a urea reactor, a stripper, a carbamate condenser, an additional pre-stripper placed between the urea reactor and the stripper, a flash vessel additionally installed between the stripper and the carbamate condenser, or to pipelines between any of such equipment.

An object of the present invention concerns improving the efficiency of high pressure urea plants. This objective can be accomplished by using a virtually water-free off-gas stream consisting predominantly of ammonia and carbon dioxide obtained from a high-pressure melamine plant in a high pressure section of a urea stripping plant. This results in an increased efficiency compared to supplying a water-containing carbamate stream from the melamine plant to a urea plant.

Yet another related object is to avoid a requirement for subjecting the off-gas stream from a melamine plant to absorbing or concentrating steps before going into the urea plant. This is accomplished in the present invention because the off-gas stream can already be virtually water-free and has a sufficiently high pressure.

A still further object is to obtain enhanced energy efficiencies in the production of urea. This can be accomplished with the present invention because the extra heat released in condensing the off-gas stream from the high-pressure melamine plant can be reclaimed and used to produce additional (low pressure) steam.

Figure 1:
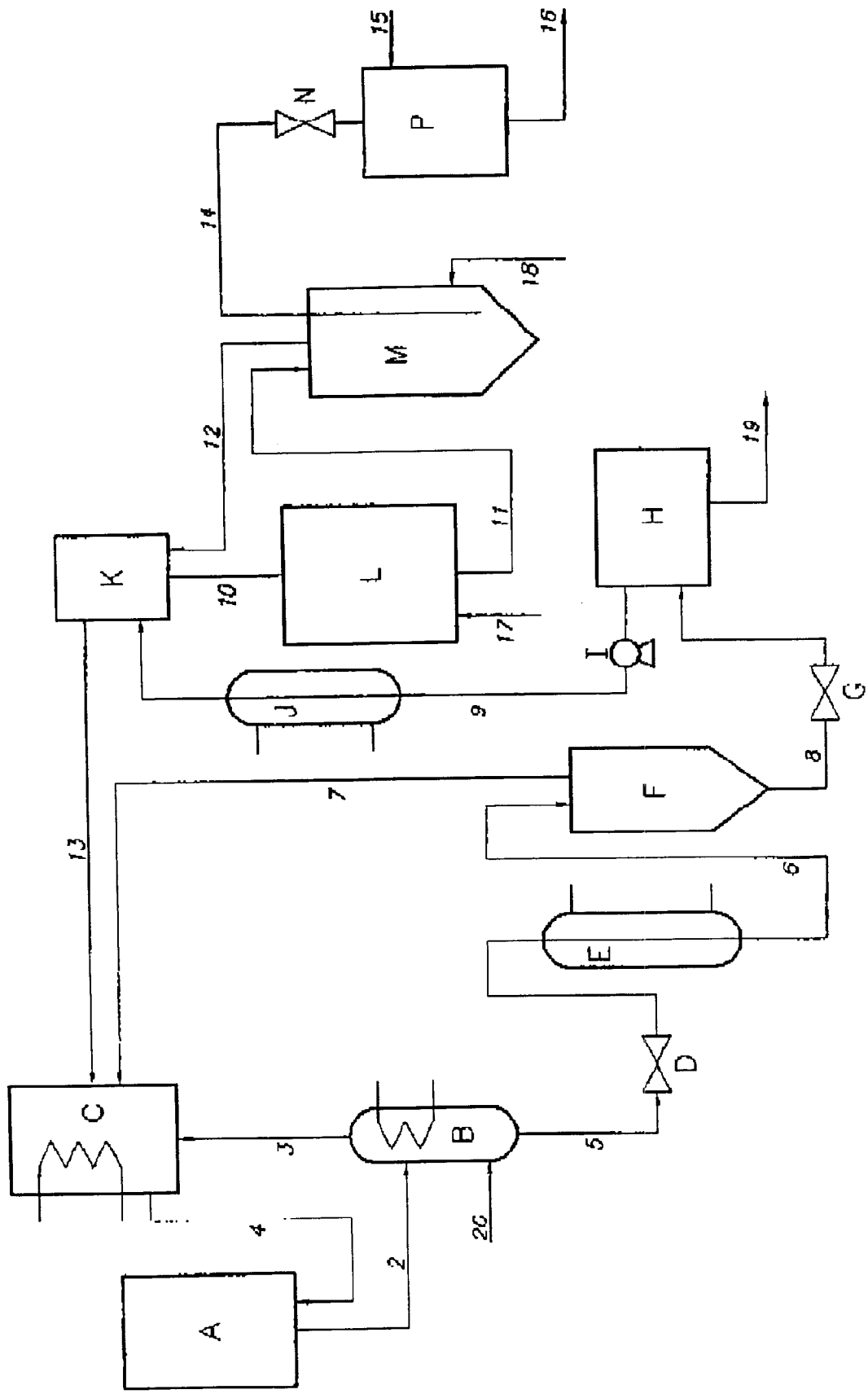
FIG. 1 is a flow diagram of urea and melamine synthesis with recycle of off-gas from the high pressure melamine plant to the carbamate condenser of the urea plant in accordance with the present invention.

DETAILED DESCRIPTION OF THE PRESENTLY PREFERRED EXEMPLARY EMBODIMENTS OF THE INVENTION

The present invention concerns the preparation of urea in a urea stripping plant having at least one high-pressure section in which an off-gas stream released during the high-pressure synthesis of melamine is supplied to at least one high-pressure section of the urea stripping plant, wherein the off-gas stream consists essentially of ammonia and carbon dioxide.

In the most simple, and preferred embodiments of the present invention the off-gas stream is supplied to a carbamate condenser in the high-pressure section of the urea stripping plant or to the line between the stripper and the carbamate condenser.

The pressure of this off-gas stream supplied from the high-pressure melamine plant is generally above about 12.5 MPa. In general, the pressure is below about 80 MPa, preferably below about 40 MPa and more preferably below about 20 MPa. In particular, the pressure of the off-gas stream coming from the high-pressure melamine plant is about 0 to about 10 MPa, particularly about 0–3 MPa and more specifically about 0–2 MPa higher than the pressure in the urea reactor. The temperature of this off-gas stream generally is above 160° C., and preferably above 175° C. The temperature of this off-gas stream is generally below 285° C., preferably below 275° C. and more preferably below 235° C.

As contemplated herein, a urea stripping plant generally means a urea plant in which the decomposition of the ammonium carbamate that has not been converted into urea and the expulsion of carbon dioxide and the usual excess ammonia are conducted at a pressure which is substantially equal to the pressure in the synthesis reactor. This decomposition/expulsion takes place in a stripper, whether or not with addition of a stripping medium. In a stripping process, carbon dioxide, ammonia or both can be used as a stripping gas before these components are fed to the synthesis reactor. This stripping takes place in a stripper which can be installed downstream of the reactor. The solution emerging from the urea reactor contains urea, ammonium carbamate, water and also ammonia and carbon dioxide. The solution can be stripped by applying additional heat. The solution can also be stripped by using thermal stripping techniques in which the ammonium carbamate is decomposed and the ammonia and carbon dioxide present are removed from the urea solution solely through the addition of heat. The ammonia and carbon dioxide containing streams coming from the stripper are returned to the reactor via a carbamate condenser. The reactor, the stripper and the carbamate condenser are among the more important components of the high-pressure section of the urea synthesis.

In a urea stripping plant the synthesis reactor is preferably operated at a temperature of about 160 to about 220° C. and at a pressure of about 12.5 to about 17.5 MPa. The N/C ratio in the synthesis in a stripping plant is typically between about 2.5 and about 4.

The present invention can thus be applied to widely used methods for the preparation of urea via urea stripping processes, such as ones described in European Chemical News, Urea Supplement, of Jan. 17, 1969, pages 17–20, the complete disclosure which is incorporated herein by reference. In this process the urea synthesis solution is formed in the synthesis zone at a high temperature and pressure, and, while heat is added, is subjected to a stripping treatment at the synthesis pressure by being contacted countercurrently with gaseous carbon dioxide. In this stripping operation, the greater part of the ammonium carbamate present in the solution is decomposed into ammonia and carbon dioxide. These decomposition products are then expelled from the solution in gaseous form and discharged together with a small amount of water vapor and the carbon dioxide used for stripping. Such a stripping treatment can be effected using carbon dioxide (gas) as the stripping medium as described for example in U.S. Pat. No. 3,356,723, the complete disclosure of which is incorporated by reference. Stripping can also be effected using the thermal stripping technique, or it can be conducted using gaseous ammonia as the stripping gas. Still further, the stripping can be conducted using a combination of the above-mentioned stripping techniques. The gas mixture obtained from the stripping treatment is for more than 95% condensed and adsorbed in a carbamate condenser. The ammonium carbamate which is thereby formed is transferred to the synthesis zone for urea formation. The gas mixture which is not condensed and absorbed may comprise for example inert gases. The urea synthesis can be carried out in one or two reactors. For example, pure ammonia and carbon dioxide can be used in a first reactor. A mixture of pure ammonia and carbon dioxide plus recycled ammonia and carbon dioxide, or recycled ammonia and carbon dioxide alone, can be used in a second reactor. By preference, the synthesis is carried out in one reactor. Likewise, the stripping of the urea synthesis solution with the aid of a gaseous stripping medium can be carried out in more than one stripper.

The carbamate condenser can, for example, be a so-called submerged condenser, such as described in NL-A-8400839, the complete disclosure of which is incorporated herein by reference. In this case the gas mixture to be condensed is fed into the shell-side space of a shell-and-tube heat exchanger, into which a dilute carbamate solution is also fed. The released heat of dissolution and condensation is discharged with the aid of a heat absorbing fluid medium flowing through the tubes. For example a suitable fluid medium is water in which case it can be converted into low-pressure steam for use elsewhere in the process or the plant. The submerged condenser may be installed horizontally or vertically. However, it is particularly advantageous to carry out the condensation in a horizontally positioned submerged condenser because residence time of the liquid in the condenser is generally longer compared with a vertically positioned submerged condenser. This results in the formation of urea, which raises the boiling point, so that the difference in temperature between the urea-containing carbamate solution and the cooling medium increases. As a result, better heat transfer is achieved. A so-called pool condenser is an exemplary submerged condenser, and one is described, for example, in Nitrogen No. 222, July–August 1996, pp. 29–31, the complete disclosure of which is incorporated by reference.

The condensation zone and the synthesis zone can, if desired, be combined in one apparatus as described for example in NL-A-1000416, the complete disclosure of which incorporated by reference. In the latter instance, the formation of ammonium carbamate and urea from carbon dioxide and ammonia can be carried out at a pressure of about 12.5 to about 35 MPa in a urea reactor. The urea reactor can have a horizontal positioned condensation zone and heat exchanger. An exemplary such urea reactor is a so-called pool reactor as described, for example, in Nitrogen No. 222, July–August 1996, pp. 29–31. Ammonia and carbon dioxide are fed to the urea reactor and are largely condensed and absorbed in the urea synthesis solution. A substantial part of the heat released by the exothermic condensation is recovered using a heat exchanger by which steam is produced. The residence time of the urea synthesis solution in the urea reactor is selected so that at least 85% of the theoretically feasible amount of urea is obtained. In general, the urea synthesis solution is then processed into a urea solution or solid urea.

After the stripping operation the stripped urea synthesis solution is expanded in several steps to a low pressure and concentrated through evaporation and the urea melt thus obtained can be entirely or partly transferred to a "tied-in" melamine plant for melamine synthesis. Such an urea and melamine operation can be characterized as an integrated operation.

Urea, urea plants and processes are, in general, described in Meessen et al., Urea, Ullmann's Encyclopedia of Industrial Chemistry, Volume A27, pages 333–365 (1996), including the references cited therein, the complete disclosures of which are incorporated herein by reference.

Urea is the preferred raw material for the preparation of melamine. The urea is preferably used in the form of a melt. Ammonia and carbon dioxide are byproducts formed during the preparation of melamine, which proceeds according to the following reaction equation:

The melamine preparation can be carried out at a pressure above 12.5 MPa and generally below 80 MPa, preferably below 40 MPa and more preferably below 20 MPa, without a catalyst being present. The temperature of the reaction can vary, and in general can be between about 300° C. and about 500° C., but is preferably between about 350° C. and about 425° C.

A plant for the preparation of melamine suitable for practicing the present invention can, for example, include a urea scrubber, a reactor, whether or not combined with a gas-liquid separator or with a separate gas liquid separator, optionally an after-reactor or aging tank arranged downstream thereof and a product cooler/product working-up section. Melamine, melamine synthesis and melamine plants are generally described in Crews et al., Melamines and Guanamines, Ullmann's Encyclopedia of Industrial Chemistry, Volume A16, pages 171 to 185 (1990), including references, the complete disclosures of which are hereby incorporated by reference.

In one embodiment of the present invention, melamine is prepared from urea in a plant comprised of, for example, a urea scrubber K, a reactor L for melamine preparation, a gas/liquid separator M and a product cooler P. Optionally an after-reactor or aging tank is installed between M and P.

In this embodiment the urea synthesis effluent obtained from the high-pressure section of a urea stripping plant is discharged via line 5 and expanded through expansion valve D, resulting in the decomposition of residual ammonium carbamate and the formation of a gas-liquid mixture. That mixture is then introduced into heater E in which a further decomposition of carbamate takes place. From heater E, the mixture is introduced via line 6 to a gas-liquid separator F. The gas phase separated in separator F, consisting primarily of ammonia and carbon dioxide, is recycled to the carbamate condenser C. In a urea plant more than one heater E and gas-liquid separator F may exist.

The urea product stream is discharged from the bottom of separator F via line 8 and further expanded through a second expansion valve G before being fed to a evaporator (not shown) and thereafter to a molten urea tank H. The molten urea may be removed therefrom via line 19, or, for melamine synthesis, it is pumped through line 9 by pump I through a heater J to urea scrubber K.

The urea melt is fed to the urea scrubber K at a pressure above 12.5 MPa and generally below about 80 MPa, preferably below about 40 MPa and more preferably below about 20 MPa, and at a temperature above the melting point of urea. Although not shown in detail, the urea scrubber K can be provided with a cooling jacket to ensure extra cooling. The urea scrubber K can also be provided with internal cooling means. In the urea scrubber K the liquid urea comes into contact with reaction gases from the gas-liquid separator M arranged downstream of the reactor L. The reaction gases consist of carbon dioxide and ammonia and, in addition, generally contains an amount of melamine vapor. The molten urea scrubs the off-gas and the melamine is carried back to the reactor L. The off-gases obtained from the scrubber consist predominantly of ammonia and carbon dioxide. The off-gases are removed from the top of the urea scrubber K and returned to the high-pressure section of a urea plant, in which urea is prepared via the stripping process, as a raw material in urea production. The pressure of the off-gas stream is generally virtually equal to the pressure in the melamine reactor L and in general is above about 12.5 MPa. The pressure is generally 0–10 MPa higher, preferably 0–3 MPa higher, and more preferably 0–2 MPa higher than in the urea reactor. The temperature of this gas stream is preferably between about 175° C. and 235° C.

The preheated urea is withdrawn from the urea scrubber K and is fed, together with the scrubbed-out melamine, via for example a high pressure pump (non-shown in detail), to the reactor L, which has a pressure above 12.5 MPa and generally below 80 MPa, preferably below 40 MPa and more preferably below 20 MPa. The urea melt may also be transferred to the melamine reactor via line 10 with the aid of gravity by placing the urea scrubber K above the reactor L, as shown in the Figures.

The molten urea is subjected to heat and pressure conditions in the melamine reactor L to convert the urea into melamine, carbon dioxide and ammonia. In general, the temperature is in a range of about 300° C. to about 500° C., and is preferably about 350° C. to 425° C. The pressure is above about 12.5 MPa but generally below about 80 MPa, preferably below about 40 MPa and more preferably below about 20 MPa.

Ammonia can be dosed, e.g. supplied to the reactor L via line 17. The ammonia supplied to the melamine reactor can, for example, function as a purifying agent to prevent clogging of the reactor bottom or to avoid the formation of melamine condensation products such as melam, melem and melon or, due the manner and locus of its introduction, to promote mixing in the reactor L. The amount of ammonia supplied to the reactor is about 0 to about 10 mol per mol urea, preferably 0–5 mol ammonia, although, in particular, about 0.1 to about 2 mol ammonia per mol urea can be used. The carbon dioxide and ammonia formed during the reaction and the additional ammonia supplied collect in a separation section. The separation section can, for example, be a section in the top of the melamine reactor, or, for instance, a separator M installed downstream of the reactor as shown in the Figures. The carbon dioxide and ammonia are separated from the liquid melamine in the form of a gas mixture. That gas mixture is fed to the urea scrubber K to remove entrained melamine vapor and to preheat the urea melt. The liquid melamine is withdrawn from the melamine reactor L and can, for example, be transferred via line 11 to gas-liquid separator M and then to a product cooler P.

In the gas-liquid separator M the liquid melamine may once again contacted with about 0.01 to about 10 mol ammonia per mole of melamine and preferably about 0.1 to about 2 mol ammonia per mole of melamine, introduced e.g. through line 18. The residence time in the gas-liquid separator M is generally between 1 minute and 10 hours, but is preferably between 1 minute and 3 hours. The pressure in the gas-liquid separator M is, in general, virtually the same as in the reactor where urea is converted into melamine or it may be lower. The temperature may be higher or lower than the reactor temperature, and will be preferably between 200–500° C., and in particular between 330–440° C. The liquid melamine present in the gas-liquid separator M is discharged from the gas-liquid separator M and transferred via line 14, through expansion valve N to a product cooler P. The liquid melamine in the product cooler P is cooled by being contacted with a cooling medium as described in, for example, U.S. Pat. No. 4,565,867 or U.S. Pat. No. 5,514,796, the complete disclosures of which are incorporated herein by reference. The cooling medium is preferably ammonia, such as liquid ammonia that is introduced e.g. through line 15. Alternatively, the pressure and temperature can be selected such that the evaporation of ammonia dissolved in the melted melamine is used to cool the melamine as described in WO-A-97/20826, the complete disclosure of which is incorporated herein by reference. The melamine is converted into a powder in the process and is discharged, from the cooling unit through line 16 in the bottom of the product cooler P.

When an after-reactor or an aging tank is used the liquid melamine is once again contacted with about 0.01 to about 10 mol ammonia per mol of melamine and preferably about 0.1 to about 2 mol ammonia per mol of melamine. The residence time in the after-reactor or in the aging vessel is generally between 1 minute and 10 hours, but is preferably between 1 minute and 3 hours. The temperatures and the pressure in the after-reactor or aging vessel are, in general, within the same range as described for the gas/liquid separator. It is preferred to use a relatively low temperature.

An evaporation step can be provided by installing an evaporator between the gas-liquid separator and the product cooler. The melamine is converted in the evaporation step into gaseous melamine whereby the byproducts, such as melam, remain behind in the evaporator. The amount of by-product impurities in the melamine is thereby reduced. As a consequence, melamine having very high purity is thus obtained. Further ammonia can, if desired, be supplied during the evaporation step. The gaseous melamine is then cooled afterwards in the product cooler with the selected cooling medium, such as ammonia or the like.

The off-gas from the melamine plant can be introduced into a high pressure section of the urea stripping plant. The section receiving the gas mixture can, for instance, be at any locus which is situated in a high-pressure section from the stripper up to and including the urea reactor itself. Thus, the off-gas stream from the high-pressure melamine process can for example be fed to a urea reactor, to a stripper, to a carbamate condenser, to a pre-stripper additionally placed between the urea reactor and the stripper, to a flash vessel additionally installed between the stripper and the carbamate condenser, or to pipelines between these.

FIG. 1 illustrates a first embodiment in which the off-gas stream coming from a high pressure melamine process is fed via line 13 to the carbamate condenser C of the high pressure urea plant. In this embodiment, as in the other embodiments of this invention, line 13 may include one or more control values (not shown in particular). According to this process, no absorption and/or concentration step of the off-gas stream coming from the melamine plant is necessary because the gas stream is already virtually water-free and has a sufficiently high pressure. Example 1, below provides a more detailed explanation of this embodiment of the invention. As will be appreciated, an advantage of this embodiment and the embodiments of FIGS. 3 and 5, discussed below, as compared to the embodiments of FIGS. 2 and 4–6, is that the advantages of feeding the off-gas stream from a melamine plant directly to a high pressure section of the urea plant can be realized without the potentially high cost of additional installation of vessels or other components in the plant.

Figure 2:
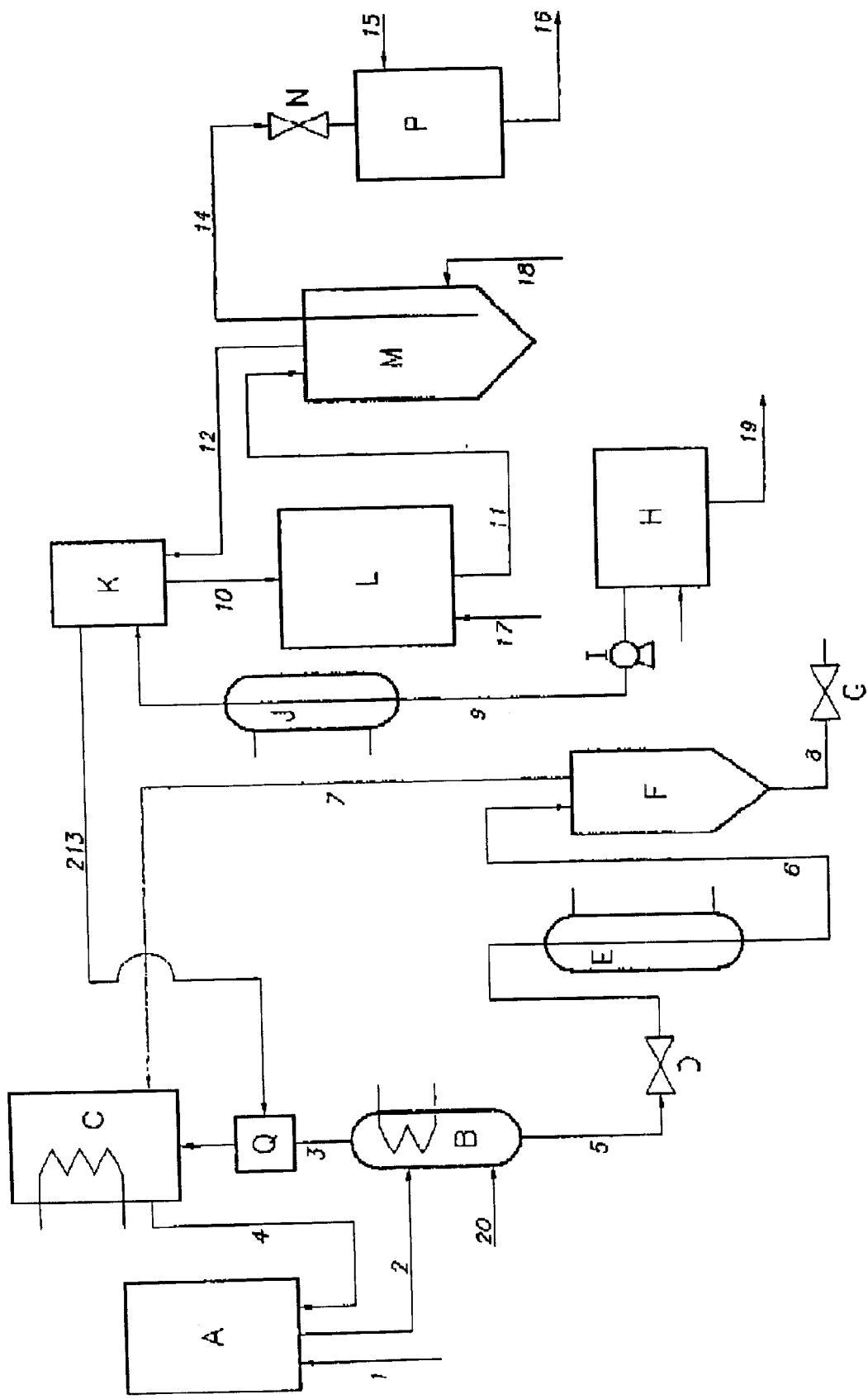
FIG. 2 is a flow diagram of urea and melamine synthesis with recycle of off-gas from the high pressure melamine plant to a flash vessel installed between the stripper and the carbamate condenser of the urea plant in accordance with the present invention.

FIG. 2 illustrates another embodiment in which the off-gas stream coming from a high pressure melamine process is fed via line 213 to a flash vessel Q additionally installed between the stripper B and the carbamate condenser C. This has an advantage if the pressure in the melamine process is substantially higher than the pressure in the urea process.

Figure 3:
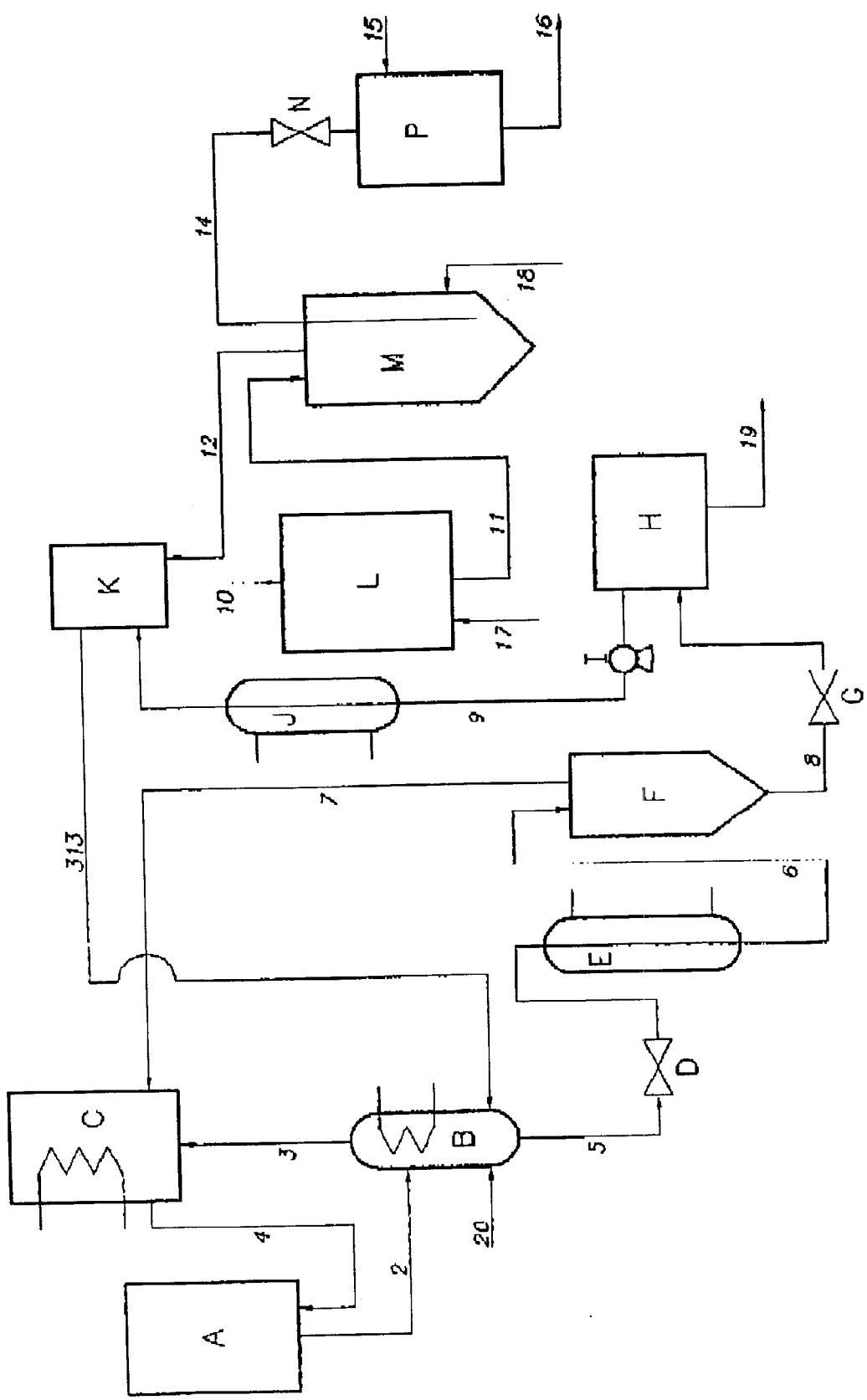
FIG. 3 is a flow diagram of urea and melamine synthesis with recycle of off-gas from the high pressure melamine plant to the stripper of the urea plant in accordance with the present invention.

FIG. 3 illustrates another embodiment in which the off-gas stream coming from the high pressure melamine process is fed via line 313 to the main stripper B in a high pressure urea plant. The advantage is that the off-gas stream is used as a stripping gas with additionally recovery of heat. The flow through the urea and melamine plants in this exemplary embodiment is otherwise as described above with reference to FIG. 1.

Figure 4:
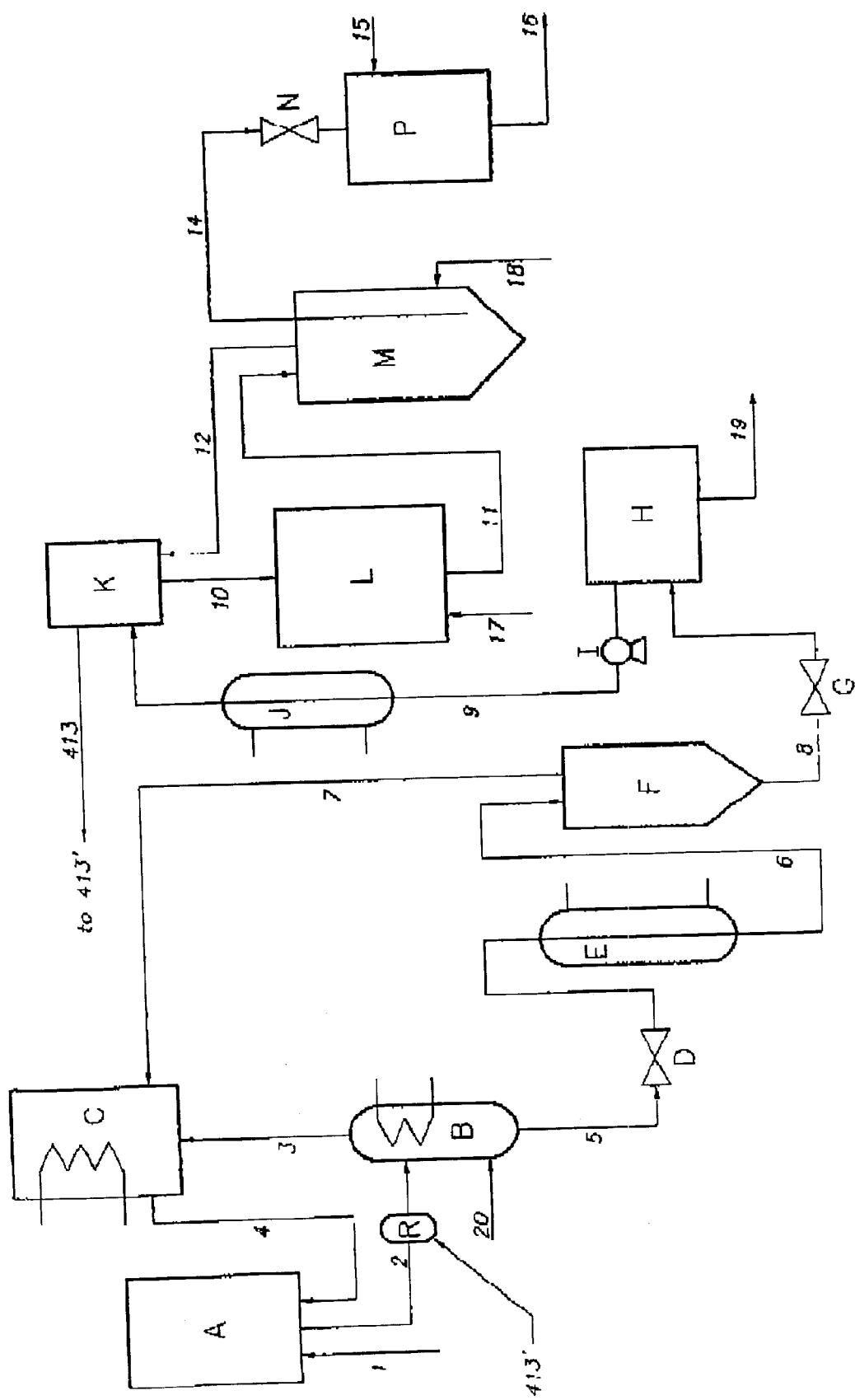
FIG. 4 is a flow diagram of urea and melamine synthesis with recycle of off-gas from the high pressure melamine plant to a pre-stripper installed between the urea reactor and the stripper of the urea plant in accordance with the present invention.
Figure 6:
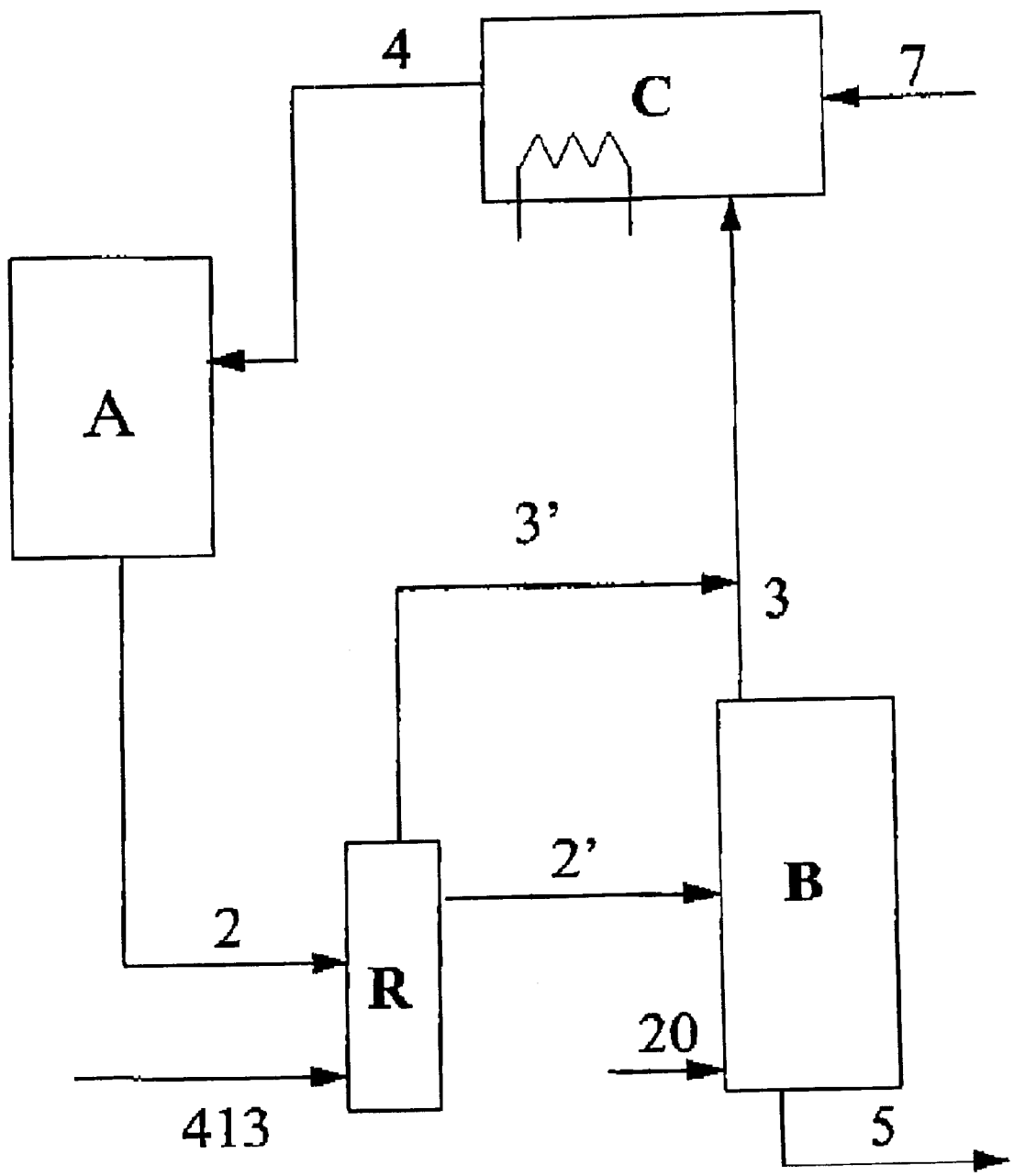
FIG. 6 depicts in greater detail off-gas stream feed to a high pressure pre-stripper in a urea plant in accordance with the present invention.

In another embodiment of the process, the off-gas stream from the melamine process is fed to a pre-stripper additionally installed between the urea reactor A and a main stripper B as shown in FIGS. 4 and 6. In this embodiment, the urea synthesis solution is stripped in the pre-stripper R with the aid of the off-gas stream supplied from the high-pressure melamine process via line 413. Again, the off-gas stream consists predominantly of ammonia and carbon dioxide. This results in an extra high-pressure-steam saving and in an improved stripping effect. In addition, it was found that extra steam production is obtained in the carbamate condenser C. The pre-stripper R is, by preference, an adiabatically operable pre-stripper. The latter is an advantage, and particularly so if the melamine plant and the urea plant are highly tied-in. Plants that are highly tied-in means that a relatively large amount of the urea produced is used by the melamine plant, for example is more than 50% of the urea produced in the urea stripping plant is used for melamine production, more in particular more than 80%. It will be appreciated that "tied in" melamine and urea plants of the present invention are not restricted to this embodiment.

Off-gas stream feed to the high pressure pre-stripper R in a urea plant is depicted in greater detail in FIG. 6. As in FIG. 4, A represents a urea reactor in which urea is prepared from ammonia and carbon dioxide. A urea synthesis solution consisting of urea, ammonium carbamate, water and ammonia is supplied to pre-stripper R via line 2. An off-gas stream consisting predominantly of ammonia and carbon dioxide comes from the high-pressure melamine plant via line 413 and partly strips the urea synthesis solution in B. The urea synthesis solution is transferred to the main stripper B via line 2' where the urea synthesis solution is stripped with the stripping medium supplied via line 20. In this operation the urea synthesis solution is separated into a gas stream and a urea solution. This urea solution is discharged via line 5 for further processing. The gas stream coming from the stripper via line 3, consisting predominantly of ammonia and carbon dioxide, is combined with the gas stream coming from the pre-stripper R via line 3', which also consists predominantly of ammonia and carbon dioxide, and jointly fed to the carbamate condenser C. The liquid ammonium carbamate solution coming from the carbamate condenser is transferred to the urea reactor A via line 4.

Figure 5:
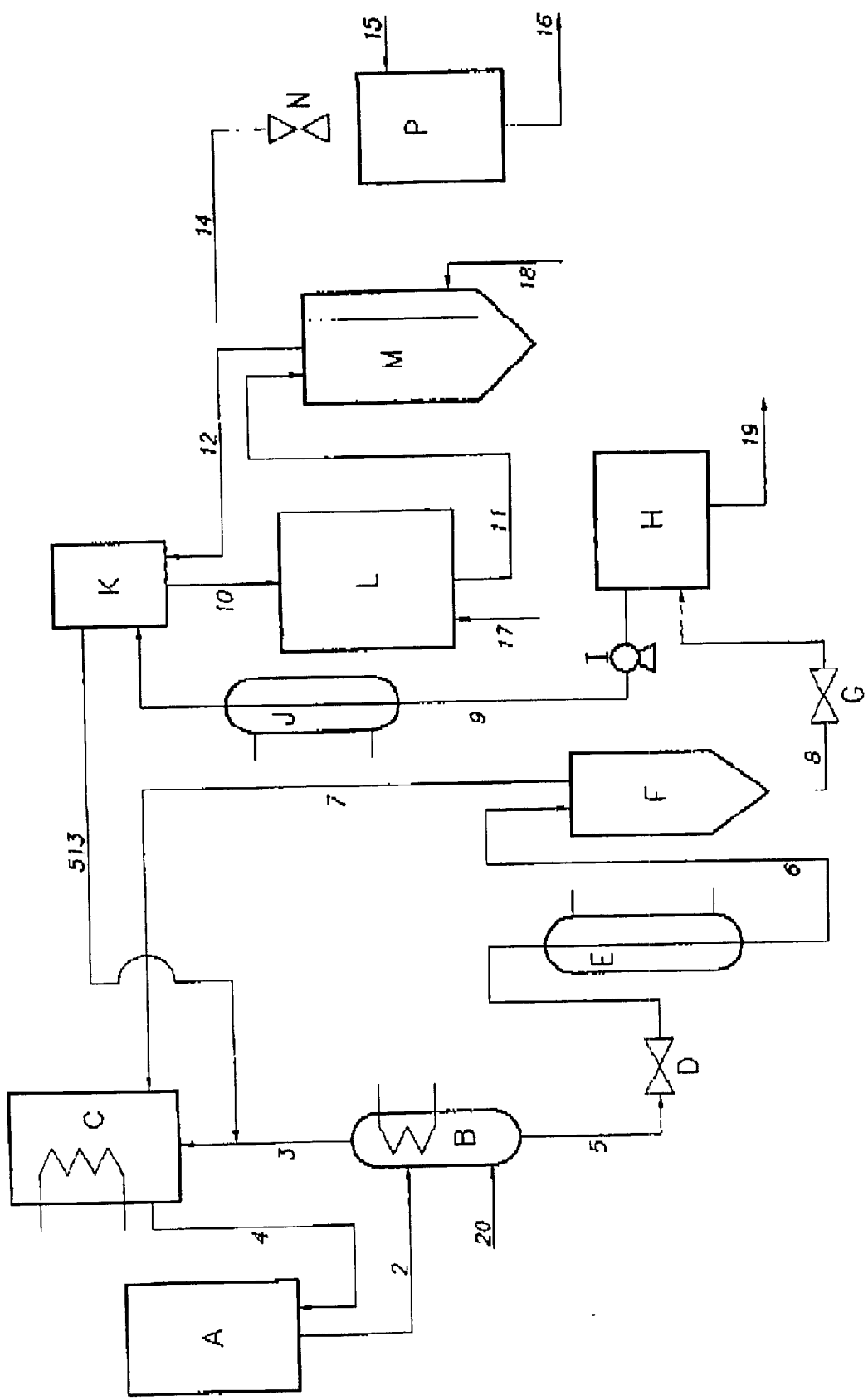
FIG. 5 is a flow diagram of urea and melamine synthesis with recycle of off-gas from the high pressure melamine plant directly into a high pressure line of the urea plant.

FIG. 5 illustrates another embodiment in which the off-gas stream coming from a high pressure melamine process is fed via line 513 directly to a high pressure line in a high pressure urea plant as illustrated, the line 3 between B and C is preferably a high pressure line in this regard. The flow through the balance of the urea and melamine plants in this exemplary embodiment is the same as described above with reference to FIG. 1.

Urea and melamine production, including the introduction of gas consisting predominately of carbon dioxide and ammonia from a high pressure melamine plant into a high pressure section of a urea plant, are described in Netherlands Patent Applications 1003923 and 1004475, filed, respectively on Aug. 30, 1996 and Nov. 8, 1996, the complete disclosures of which are incorporated herein by reference.

EXAMPLES

The invention will be explained in detail with reference to the following examples.

Example 1

A gas consisting predominantly of ammonia and carbon dioxide with an N/C ratio of 2.7 at a temperature of 200° C. and a pressure of 15 MPa emerges from a high-pressure melamine synthesis with a capacity of 5 tons of melamine per hour from the top of the melamine scrubber. This stream is fed directly to the carbamate condenser of a 1200-ton/day urea stripping plant in which the pressure is 14 MPa, as a result of which 7.6 tons less high-pressure steam (of 2.7 MPa) per hour need to be imported and 1.3 tons less low-pressure steam (of 0.4 MPa) are exported from the urea plant compared with the working-up of the carbamate from a conventional tie-in stage of a 0.7 MPa low-pressure melamine plant. In the conventional tie-in stage the carbamate stream coming from the melamine plant is concentrated to make it suitable for use in the urea stripping plant. In addition, 20 tons of high-pressure steam (of 2.7 MPa) per hour are saved in the tie-in stage of the present invention, but an extra 5.5. tons of high-pressure steam (of 2.7 MPa) are needed in the evaporation section of the urea plant. The overall saving achieved is 5.5 tons of high-pressure steam (of 2.7 MPa) per ton of melamine, while the export of low-pressure steam (of 0.4 MPa) is reduced by 1.4 tons per ton of melamine.

Example 2

A gas consisting predominantly of ammonia and carbon dioxide with an N/C ratio of 2.7 at a temperature of 200° and a pressure of 15 MPa emerges from a high-pressure melamine synthesis with a capacity of 5 tons of melamine per hour from the top of the melamine scrubber. This stream is directly fed to a high-pressure section of a urea stripping plant. In this example, the steam is fed to an adiabatically operated pre-stripper installed between the urea reactor and the $CO_2$ stripper. As a result, 2.2 tons less high-pressure steam (of 2.7 MPa) are needed in the $CO_2$ stripper and 2.4 tons less low-pressure steam (of 0.4 MPa) are generated in the carbamate condenser in comparison to Example 1.

What is claimed is:

1. A urea stripping plant for the preparation of urea, the plant having at least one high-pressure section operating at a pressure above 12.5 MPa comprising at least a urea reactor, a stripper, a carbamate condenser, and fluid flow lines interconnecting the same, and a melamine off-gas line for supplying an off-gas stream released during the high-pressure process for making melamine, the high-pressure process operating at a pressure at least equal to that of the high pressure section, to the high-pressure section, wherein said gas stream consists essentially of ammonia and carbon dioxide.

2. A plant according to claim 1, wherein said at least one high-pressure section to which the gas stream is supplied further comprises at least one of a pre-stripper installed between the reactor and the stripper, a flash vessel installed between the stripper and the carbamate condenser, and pipelines between any thereof.

3. A plant according to claim 2, wherein the high-pressure section comprises an adiabatically operated pre-stripper installed between a urea reactor and a stripper.

4. An apparatus for urea and melamine synthesis comprising:

a urea plant including a high pressure section operating at a pressure of at least 12.5 MPa having a urea reactor, a stripper, a carbamate condenser, and fluid flow lines interconnecting the same;

a high-pressure melamine plant, the high-pressure melamine plant operating at a pressure at least equal to that of the high pressure section, including a urea scrubber for receiving urea melt, a melamine reactor, and a product cooler for generating powdered melamine, and fluid flow lines interconnecting the same;

and an off-gas supply line for supplying off-gas from at least one of the melamine reactor and the urea scrubber directly to the high pressure section at a pressure at or above a pressure prevailing in the high pressure section.

5. An apparatus according to claim 4, wherein the high-pressure section to which the off-gas stream is supplied further comprises at least one of a pre-stripper installed between the reactor and the stripper, a flash vessel installed between the stripper and the carbamate condenser, and pipelines between any thereof.

6. An apparatus according to claim 5, wherein the off-gas supply line is operatively coupled to an adiabatically operated pre-stripper installed between the urea reactor and the stripper.

* * * * *